(12) United States Patent
Kamerling et al.

(10) Patent No.: US 6,282,449 B1
(45) Date of Patent: Aug. 28, 2001

(54) METHOD AND DEVICE FOR CAUSING THE EYE TO FOCUS ON A NEAR OBJECT

(76) Inventors: William Kamerling; Joseph M. Kamerling, both of 423 Clements Bridge Rd., Barrington, NJ (US) 08007

( * ) Notice: Subject to any disclaimer, the term of this patent is extended or adjusted under 35 U.S.C. 154(b) by 0 days.

(21) Appl. No.: 09/262,562

(22) Filed: Mar. 4, 1999

Related U.S. Application Data

(63) Continuation-in-part of application No. 09/176,673, filed on Oct. 21, 1998, now abandoned.

(51) Int. Cl.[7] .................................................... A61N 1/36
(52) U.S. Cl. ................................................................ 607/53
(58) Field of Search ................................. 607/2, 33, 53, 607/61, 62; 600/546

(56) References Cited

U.S. PATENT DOCUMENTS

| | | | |
|---|---|---|---|
| 5,496,355 | * 3/1996 | Lipsky | 607/53 |
| 5,702,431 | * 12/1997 | Wang et al. | 607/61 |
| 5,749,909 | * 5/1998 | Schroeppel et al. | 607/61 |
| 5,782,894 | 7/1998 | Israel . | |
| 5,814,095 | * 9/1998 | Muller et al. | 607/57 |
| 5,925,068 | * 7/1999 | Kroll | 607/29 |

* cited by examiner

*Primary Examiner*—Kennedy Schaetzle
(74) *Attorney, Agent, or Firm*—Stuart E. Beck

(57) ABSTRACT

An improved method and subconjunctival device for causing the eye to focus on a near object. The device automatically changes the focal length of the eye in response to a changing of the length of the medial rectus muscle or the inferior rectus muscle so that the eye can focus on a near object. The device is powered by a rechargeable battery and includes an electrode for stimulating the ciliary muscle as the length of the medial rectus muscle or the inferior rectus muscle changes.

10 Claims, 1 Drawing Sheet

METHOD AND DEVICE FOR CAUSING THE EYE TO FOCUS ON A NEAR OBJECT

RELATED PATENT APPLICATIONS

This patent application is a continuation in part of U.S. patent application Ser. No. 09/176,673, filed Oct. 21, 1998, now abandoned.

FIELD OF THE INVENTION

This invention relates to an improved method and apparatus for assisting an eye to focus on an object, and more particularly to an improved method and an apparatus that is implanted in the body.

BACKGROUND OF THE INVENTION

It is well known that an aging lens precludes or diminishes a person's capacity to focus on near objects. Focus is accomplished by changing the curvature of the lens and the angular relation of the eyes to each other in accordance with the distance of the observed object to the eye.

The change in curvature of the lens, called "Accommodation" is controlled by the circular fibers of the ciliary muscle which is an annulus that is connected to the lens by the zonules. When the ciliary muscle is relaxed, the lens is flattened, i.e., it has less curvature. Thus, distant objects are in focus.

On the other hand, contraction of the ciliary muscle will cause the zonules to relax and the lens to thicken, i.e., it has more curvature, thereby shortening its focal distance to accommodate the viewing of a near object.

Accommodation causes the angular relation of the eyes to change such as by rotating them inwardly so that they turn toward the near object and so that they turn down. The inward rotation which is caused by the medial rectus muscles is called "Convergence." The downward turning which is caused by the inferior rectus muscles does not have a specific name.

The amount of Convergence caused by an Accommodating lens is called the Accommodation—Convergence Ratio:

$$\frac{AC}{A}$$

where Accommodation is measured in diopters and Convergence is measured in meter angles (m.a.).

The Accommodation—Convergence Ratio which is about 4:1 is constant throughout life.

On the other hand, when the medial rectus muscle causes the eye to turn toward a near object, the lens accommodates a given amount. This is the Convergence—Accommodation Ratio:

$$C/A$$

The Convergence—Accommodation Ratio varies over a lifetime. For young people, the ratio is about 4 m.a. per diopter. However, as a result of ageing the lens gradually becomes less elastic and the ciliary muscle weakens so that the ciliary muscle is not strong enough to cause the lens to adequately accommodate so that when the eyes converge 4 m.a., the accommodation is less than one diopter and there is a failure to focus. The reduction of the ability of the lens to accommodate is called presbyopia.

Therefore, as a person ages, more stimulation must be applied to the ciliary muscle so that it can contract and maintain the 1:4 ratio.

As explained in Kamerling U.S. Pat. No. 4,603,697, which issued Aug. 5, 1986, the content of which is hereby incorporated in its entirety by reference, the inability of the eye to focus on near objects can be compensated for by the use of an implanted electrode that can assist the eye to maintain focus. The electrode stimulates the ciliary muscle to constrict and thereby thicken the lens to increase its curvature so that it focuses on a near object thereby keeping the presbyopes in focus.

The system described in the Kamerling patent relies upon an external or internal source of power which must be energized to stimulate the ciliary muscle. That patent discloses that the stimulation can be achieved by using radio signals which are detected by an antenna.

It would be desirable if the lens could be automatically focused without external stimulation when a person changes the focus to read or see a near object.

SUMMARY OF THE INVENTION

Thus, with the foregoing in mind, the invention relates to a method for enabling the eye to focus on a near object comprising the step of applying an electrical stimulation to the ciliary muscle in response to a change in the length of the medial rectus muscle or the inferior rectus muscle.

In another aspect the invention relates to a device for enabling the eye to focus on an object. The device comprises an electrode for electrically stimulating the ciliary muscle to change the focus of the eye. It also includes another implanted means for generating an electrical signal in response to the movement of the medial rectus muscle or the inferior rectus muscle, a battery, and electrical connectors for connecting the battery, electrode and movement sensor.

DETAILED DESCRIPTION OF THE INVENTION

Figure 1:
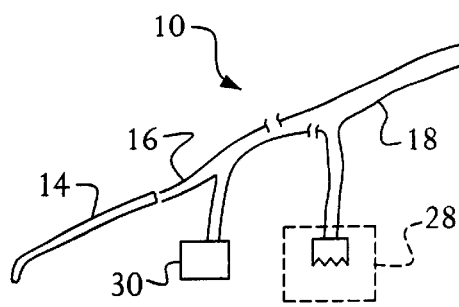
FIG. 1 is a schematic drawing of a device constructed in accordance with the invention.

Referring to FIG. 1, a device 10 constructed in accordance with a presently preferred form of the invention is seen to include an electrode 14 which is connected by thin wires 16 and 18 to an implanted rechargeable battery 24, a movement sensor 28 and a micro-chip 30.

As will be explained more completely, the rechargeable battery 24 supplies a minute voltage signal to the electrode 14 by way of the micro-chip 30 when the movement sensor 28 detects a change in the length of the medial rectus muscle.

Figure 2A:
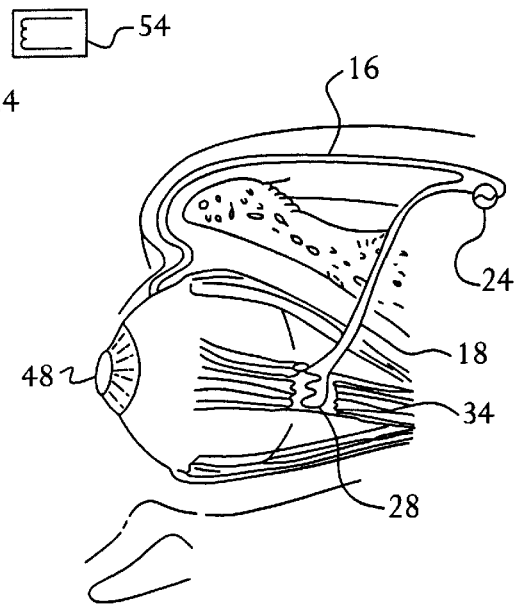
FIG. 2A is a front schematic view of the eye showing a sensor constructed in accordance with the invention connected to the medial rectus muscle.
Figure 2B:
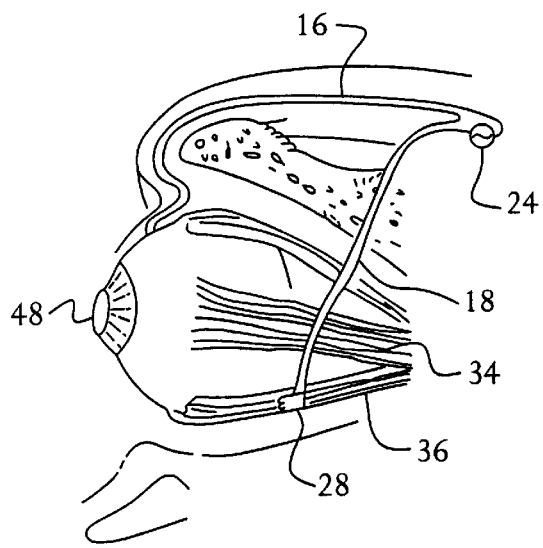
FIG. 2B is a front schematic view of the eye showing a sensor constructed in accordance with the invention connected to the inferior rectus muscle.

Referring to the FIGS. 2A and 2B, it can be seen that the motion sensor 28 is connected to the medial rectus muscle 34 (FIG. 2A) or the inferior rectus muscle 36 (FIG. 2B). The electrode 14 is inserted into the ciliary muscle 40.

As is well understood, when a person tries to view a near object, the medial rectus muscle 34 and the inferior rectus muscle 36 of each eye shortens slightly as the eyes turn in toward the object and down while the lens 48 thickens to increase its curvature and shorten its focal length.

Figure 3:
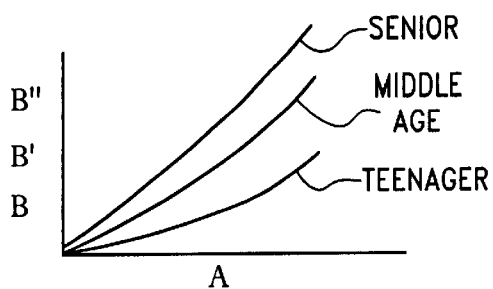
FIG. 3 is a graph showing the ratio of voltage signals necessary to accomplish the result of the invention as a person ages.

In accordance with the invention and as seen in FIGS. 2A, 2B and 3, the change in length of the medial rectus muscle 34 or inferior rectus muscle 36 is detected by the sensor 28 which sends a first low voltage signal A (FIG. 3) which is proportional to the change in medial rectus 34 or inferior rectus 36 length to electrode 14 through the micro-chip 30.

The micro-chip 30 includes a circuit (not shown) that emits a second low voltage signal B which is proportional to the first low voltage signal to stimulate ciliary muscle 40 and cause it to contract.

The contracted ciliary muscle 40 will consequently thicken the lens 48 in proportion to the change in length of the medial rectus muscle 34. Therefore, the focal length of the lens 48 is shortened and the near object is brought into focus for viewing.

When the object is removed, the medial rectus muscle 34 and inferior rectus muscle 36 relaxes, the first low voltage signal A is reduced, the ciliary muscle 40 ceases to be stimulated and the lens 48 flattens to permit viewing of distant objects.

The ratio of the second low voltage signal emitted by the micro-chip B for a given first low voltage signal A is built into the micro-chip 30 and is based on the amount of stimulation needed by the ciliary muscle. This can be determined individually for each person after examination. In the alternative it can be approximated by relying on the person's age since rate at which Accommodation—Convergence Ratio deviates from the 4:1 ratio as a person ages is known.

Further, as the person ages and the ciliary muscle 40 continue to weaken and the elasticity of the lens 48 continues to decrease, the amount of stimulation that the ciliary muscle 40 will require to thicken the lens 48 an amount sufficient to bring an object into focus will increase. Therefore, for given change in length of the medial rectus muscle 34 or inferior rectus muscle 36, and a corresponding first low voltage signal A that the change in length causes, the second low voltage signal emitted by the micro-chip 30 will have to be greater as that person ages to maintain the Accommodation—Convergence Ratio at 4:1 as seen in FIG. 3 at B' and B".

The ratio of the second low voltage signal B, B' or B" to the first low voltage signal A necessary to accommodate the weakening of the ciliary muscle and loss of elasticity of the lens can be increased by simply replacing the micro-chip 30 with one that has the preferred voltage signal ratio built into it, or the micro-chip may be remotely reprogrammed to provide the desired second low voltage signal B, B' or B" in response to a given first low voltage signal A.

Figure 4:
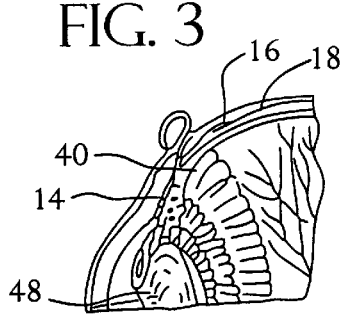
FIG. 4 is a section of the eye showing the electrode inserted in the ciliary muscle in accordance with the present invention.
Figure 5:
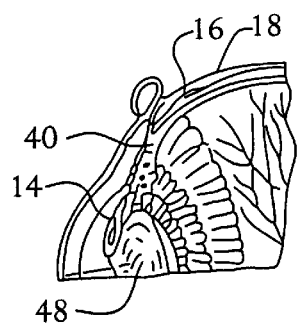
FIG. 5 is a section of the eye showing the electrode inserted over the sclera adjacent the ciliary muscle in accordance with the invention.

In its presently preferred form, the device 10 is contained entirely within the body. The electrode 14 can be inserted into the ciliary muscle as seen in FIG. 4 or the sclera adjacent the ciliary muscle as seen in FIG. 5. Hence, there are no antennae, electrodes, connecters or any other part extending through the skin.

The rechargeable battery 24 is recharged transcutaneously from time to time by magnetic induction in a manner similar to that describe in U.S. Pat. No. 5,411,537 or through a series resonant circuit such as that described in U.S. Pat. No. 5,279,292, or other similar suitable electromagnetic recharging device 54. It will be apparent when the rechargeable battery 24 requires recharging since this will be detected by the diminution and ultimate inability of the eyes to focus on near objects.

The electrode 14 of the device 10 may be surgically inserted by performing a limbal peritomy, pulling back a conjunctival tenons flap, grasping the wires 16 and 18 and the electrode 14 and inserting them through the sclera of the eye so that the electrode extends preferably into the circular fibers of the ciliary muscle 40 as seen in FIG. 4 approximately 4 millimeters behind the limbus, and then closing the conjunctiva with sutures. While insertion into the circular fibers of the ciliary muscle is preferred, the electrode could be inserted into the longitudinal fibers without impairing the operability of the device.

The rechargeable battery 24 and micro-chip 30 may be implanted subconjunctivally in which case the wires 16 and 18 can run subconjunctivally to the electrode 14.

Still further, the motion sensor 28 which may be comprised of a very thin wire can be sutured directly into or hooked onto the medial rectus muscle 34 or inferior rectus muscle 36 so that its length changes in accordance with the movement of that muscle, thereby varying the low voltage signal A applied to the micro-chip 30 and the low voltage signal B applied to the electrode 14.

The ratio of object distance to change of length of the medial rectus muscle, i.e., Convergence, is incorporated into the Accommodation—Convergence Ratio and hence is well known by those skilled in the art. Similarly, ratio of object distance to change of length of the inferior rectus muscle, is well known by those skilled in the art. Accordingly, it is a relatively straightforward process to calibrate the micro-chip 30 so that constriction of the ciliary muscle 40 and the consequent reduction in the focal length of the eye is proportional to the change in length of the medial rectus muscle 34 or the inferior rectus muscle 36.

When the device 10 is installed, the patient will be essentially unaware of its presence since it will operate to bring the lens 48 into focus automatically in response to the movement of the medial rectus or inferior muscles 34 and 36 of each eye.

The only time that the device will require attention would be when the rechargeable battery 24 requires recharging, which can be accomplished by a suitable battery recharger 54, or when the micro-chip 30 is replaced or reprogrammed.

While the invention has been described with respect to one presently preferred embodiment, it is apparent that other forms of embodiments will be obvious to those skilled in the art in view of the foregoing description. Thus, the scope of the invention should not be limited by that description, but, rather, only by the scope of the appended claims.

What is claimed is:

1. A method of causing the eye to focus on a near object: comprising the step of applying an electrical stimulation to the ciliary muscle in response to a change in the length of the inferior rectus eye muscle.

2. A method as defined in claim 1 wherein stimulation of the ciliary muscle causes the lens to thicken.

3. A method as defined in claim 2 including the steps of providing:
   an implantable sensor for the inferior rectus eye muscle, said sensor being operative to generate a signal in response to a change in the length of said eye muscle,
   implanting a means for stimulating the ciliary muscle, and said last named means being operative to stimulate the ciliary muscle in response to said signal from said sensor.

4. A method as defined in claim 3 including the steps of:

implanting a rechargeable battery, said battery being operative to provide power for said sensor and for said means for stimulating the ciliary muscles.

5. A method as defined in claim 4 wherein said battery is recharged by electromagnetic energy.

6. A method as defined in claim 1 wherein said stimulation causes the ciliary muscle to contract in proportion to the shortening of the inferior rectus eye muscle.

7. A method as defined in claim 1 wherein said stimulation prevents or treats presbyopia.

8. A method as defined in claim 4 including the step of providing means for generating a signal to stimulate said ciliary muscle in response to said signal generated by a change in the length of said inferior rectus muscle, and implanting said means for stimulating said ciliary muscle, said means for generating a signal, said battery, and said sensor being under the conjunctiva of the eye which is being focused.

9. A device for enabling the eye to focus on an object, said device comprising:

a first subconjunctivally implantable means for electrically stimulating the ciliary muscle to change the focus of the eye said first implantable means controlled by a generated electrical, a second subconjunctivally implantable means for generating said electrical signal in response to the movement of the inferior rectus eye muscle, means for providing a source of electrical energy for said device, said last named means comprising a subconjunctivally implantable battery, and said means for generating a signal, said means for providing a source of electrical energy and said means for stimulating said ciliary muscles are adapted to be disposed under the conjunctiva of the eye which is being focused.

10. A device as defined in claim 9 wherein said battery is a rechargeable battery, and means for trans-conjunctivally recharging said rechargeable battery.

* * * * *

UNITED STATES PATENT AND TRADEMARK OFFICE
CERTIFICATE OF CORRECTION

PATENT NO.   : 6,282,449 B1
DATED        : August 28, 2001
INVENTOR(S)  : William Kamerling and Joseph M. Kamerling It is certified that error appears in the above-identified patent and that said Letters Patent is hereby corrected as shown below:

Column 6,
Line 4, after "electrical", insert -- charge --.

Signed and Sealed this

Eighth Day of April, 2003

JAMES E. ROGAN
*Director of the United States Patent and Trademark Office*